(12) United States Patent
Schneider et al.

(10) Patent No.: US 12,390,091 B2
(45) Date of Patent: Aug. 19, 2025

(54) ENDOSCOPIC INSTRUMENT AND SHAFT AND INSERT FOR ENDOSCOPIC INSTRUMENT

(71) Applicant: KARL STORZ SE & Co KG, Tuttlingen (DE)

(72) Inventors: Janosz Schneider, Tuttlingen (DE); Daniel Kärcher, Tuttlingen (DE); Robin Merz, Tuttlingen (DE); Sven Schneider, Tuttlingen (DE); Tobias Unger, Tuttlingen (DE); Dominik Längle, Tuttlingen (DE); Judith Holzer, Tuttlingen (DE)

(73) Assignee: KARL STORZ SE & Co. KG, Tuttligen (DE)

( * ) Notice: Subject to any disclaimer, the term of this patent is extended or adjusted under 35 U.S.C. 154(b) by 531 days.

(21) Appl. No.: 17/747,937

(22) Filed: May 18, 2022

(65) Prior Publication Data

US 2022/0369903 A1    Nov. 24, 2022

(30) Foreign Application Priority Data

May 19, 2021 (DE) .......................... 102021112975.3

(51) Int. Cl.
| | | |
|---|---|---|
| A61B 1/00 | (2006.01) | |
| A61B 1/018 | (2006.01) | |
| A61B 17/00 | (2006.01) | |
| A61B 17/29 | (2006.01) | |

(52) U.S. Cl.
CPC ...... *A61B 1/00087* (2013.01); *A61B 1/00101* (2013.01); *A61B 1/018* (2013.01)

(58) Field of Classification Search
CPC ...... A61B 1/00101; A61B 2017/00473; A61B 2017/2931; A61B 1/00128; A61B 1/053; A61B 2017/00477; A61B 2039/1027; A61B 39/12; F16L 37/04; F16L 37/025; A61M 2039/1027
See application file for complete search history.

(56) References Cited

U.S. PATENT DOCUMENTS 3,990,727 A * 11/1976 Gallagher ............. F16L 37/252
285/148.2
2006/0264911 A1* 11/2006 Nelson .................. A61M 39/12
604/890.1

(Continued)

*Primary Examiner* — Anh Tuan T Nguyen
*Assistant Examiner* — Rynae E Boler
(74) *Attorney, Agent, or Firm* — McGlew and Tuttle, P.C.

(57) ABSTRACT

An endoscopic instrument is disclosed that includes an elongate shaft and an instrument insert releasably connected to a distal end portion of the shaft, the distal end portion of the shaft being in the form of a sleeve and a proximal end region of a base of the instrument insert being in the form of a coupling shaft, or the distal end portion of the shaft being in the form of a coupling shaft and a proximal end region of a base of the instrument insert being in the form of a sleeve, with the coupling shaft being releasably held in the sleeve and the sleeve and/or the coupling shaft at least in portions having a cross-sectional profile which is reversibly changeable for detaching the coupling shaft from the sleeve. The invention also relates to a shaft for an endoscopic instrument, and to an instrument insert for an endoscopic instrument.

13 Claims, 7 Drawing Sheets

(56) References Cited

U.S. PATENT DOCUMENTS

| | | | |
|---|---|---|---|
| 2008/0004656 A1* | 1/2008 | Livneh | A61B 18/1445 |
| | | | 606/205 |
| 2013/0138129 A1* | 5/2013 | Garrison | A61B 18/1445 |
| | | | 74/100.1 |
| 2013/0158521 A1* | 6/2013 | Sobue | A61M 39/10 |
| | | | 604/535 |
| 2020/0323553 A1* | 10/2020 | Fernandez | A61B 17/320783 |
| 2022/0249152 A1* | 8/2022 | Shimamura | A61B 18/14 |

* cited by examiner

ENDOSCOPIC INSTRUMENT AND SHAFT AND INSERT FOR ENDOSCOPIC INSTRUMENT

CROSS REFERENCE TO RELATED APPLICATIONS

This application claims priority to German Patent Application No. 102021112975.3, filed May 19, 2021, and entitled, "Endoskopisches Instrument sowie Schaft and Instrumenteneinsatz für ein endoskopisches Instrument," and is incorporated herein by reference.

TECHNICAL FIELD OF THE INVENTION

The present invention relates to an endoscopic instrument, in particular a medical endoscopic instrument, to a shaft for an endoscopic instrument, and to an instrument insert for an endoscopic instrument.

BACKGROUND OF THE INVENTION

Within the scope of an endoscopic intervention, an endoscopic instrument set, which may comprise an endoscope and one or more endoscopic instruments in particular, is guided to an operating region situated within the body through a natural body orifice or through an artificial body orifice created with the aid of an incision. To this end, endoscopic instruments have an elongate shaft, a tool being arranged at said shaft's distal end, that is to say at said shaft's end distant from the user, and said tool being able to be actuated by a handle arranged at the proximal end, that is to say the end close to the user, of the shaft via an elongate transmission element arranged in the shaft. The shaft may have a rigid or flexible form. During an endoscopic intervention, the handle remains outside of the body opening while the shaft with the tool is inserted through the body opening.

According to a common design, endoscopic instruments comprise an instrument insert which carries the tool at its distal end, and which may also comprise the transmission element, for instance a connecting rod. The instrument insert, which is also referred to as a work insert, is releasably connected to the shaft of the instrument. In this case, provision can be made for instrument inserts with different tools to be able to be connected to the shaft and be able to be detached therefrom again. In particular, the instrument is able to be taken apart for cleaning and/or sterilization purposes, with the instrument insert being detached from the shaft; further, the handle can be separated from the shaft.

For the releasable connection of the instrument insert to a distal end portion of the shaft, a connection in the style of a bayonet connection, is known. Endoscopic instruments in which a tool or an instrument insert is connectable to the distal end of a shaft in the style of a bayonet connection are disclosed in EP 0 688 187 B1 and DE 197 22 062 A1, for example. In this case, a connecting rod by means of which the tool can be actuated simultaneously represents an anti-twist device for maintaining the bayonet engagement. To this end, the connecting rod is flattened in the proximal region, with two clamping parts engaging with the flattening such that a twist of the connecting rod relative to a tubular shaft of the instrument is prevented.

Generic medical endoscopic instruments are sold commercially by KARL STORZ SE & Co. KG, for example under the trade names "ClickLine®" and "RoBi®".

SUMMARY OF THE INVENTION

It is an object of the present invention to specify an endoscopic instrument, in particular a medical endoscopic instrument, wherein an instrument insert is releasably connected to a distal end portion of a shaft of the instrument by means of a connecting mechanism, with there being, in particular, a connection without an anti-twist device or with an alternative anti-twist device. Likewise, it is an object of the present invention to specify a shaft and an instrument insert for such an endoscopic instrument.

An endoscopic instrument according to the invention is, in particular, a medical endoscopic instrument, for example a surgical endoscopic instrument for carrying out minimally invasive surgical interventions. The endoscopic instrument comprises an elongate shaft which, in particular, is designed to be inserted into a body-internal cavity of a human or animal body. The shaft preferably has a rigid or substantially rigid design and comprises an elongate shaft tube, which may represent an external shaft of the instrument; alternatively, the shaft may also have a flexible design. Further, the endoscopic instrument comprises an instrument insert that is releasably connected to a distal end portion of the shaft, in particular releasably held at the distal end of the shaft.

The instrument insert comprises a tool which is designed to carry out endoscopic manipulations in the body-internal cavity in particular and preferably a shaft-shaped base, which is also referred to as a fork. The tool may comprise two interacting tool elements, at least one of which is movable relative to the base. By way of example, the tool can be a pair of surgical scissors or gripping forceps, which have one or two tool elements that are able to pivot relative to one another and are designed as scissor parts or jaw parts, with at least one of said tool elements being mounted in articulated fashion on the base. The tool may be actuatable by way of an elongate transmission element which extends within the shaft up to the proximal end thereof and which may, for example, be designed as a connecting rod, which is connected to the at least one movable tool element in articulated fashion. The transmission element may be part of the instrument insert.

According to the invention, the distal end portion of the shaft of the endoscopic instrument is in the form of a sleeve and a proximal end region of the base of the instrument insert is in the form of a coupling shaft, with the coupling shaft being releasably held in the sleeve for the releasable connection of the instrument insert to the shaft. An alternative according to the invention provides for the proximal end region of the base of the instrument insert to be in the form of a sleeve and the distal end portion of the shaft to be in the form of a coupling shaft, which is releasably held in the sleeve for the releasable connection of the instrument insert to the shaft. The sleeve, which may also be referred to as a coupling sleeve, and the coupling shaft, which may also be referred to as a coupling pin, consequently form a coupling for releasably connecting the instrument insert to the shaft, and are accordingly designed for interaction with one another.

When the instrument insert is connected to the shaft by means of the coupling formed by the sleeve and the coupling shaft, the base and the tool are preferably arranged along a distal-side continuation of a longitudinal axis of the shaft. In particular, the base may have a longitudinal axis which is at least approximately flush with the longitudinal axis of the shaft whenever the instrument insert is connected to the shaft. The coupling shaft is preferably in the form of a hollow shaft or hollow tube, through which the transmission element can extend. In the case where the distal end portion of the shaft is in the form of a sleeve, the sleeve may represent a distal continuation or distal end portion of a shaft tube, with the transmission element being guided in the interior of the shaft tube.

Further, according to the invention, the sleeve and/or the coupling shaft at least in portions have a cross-sectional profile which is reversibly changeable for detaching the coupling shaft from the sleeve. According to the invention, the sleeve and/or the coupling shaft, in relation to the longitudinal axis of the shaft or of the base, is consequently formed in at least one portion with a changeable cross-sectional profile, and the sleeve and the coupling shaft are designed in such a way that the coupling shaft is detachable from the sleeve by changing the cross-sectional profile. In this case, the change of the cross-sectional profile may consist in a change in the shape of the cross section, that is to say a deformation of the cross-sectional profile or cross-sectional contour, and/or a change in the dimensions of the cross section, that is to say a change in the size or radius of the cross-sectional profile or cross-sectional contour. In particular, the sleeve and/or the coupling shaft may be reversibly deformable and designed in such a way that the coupling shaft can be released from the sleeve by way of cross-sectional deformation. The cross-sectional deformation by means of which the coupling is released may be brought about, in particular, by a force acting from the outside. The force acting from the outside, for example a compressive force exerted on the sleeve in the radial direction, may be exerted manually by a user. In this case, a stiffness of the sleeve or of the coupling shaft is chosen in such a way, in particular, that the compressive force can comfortably be exerted by the user using their fingers on one hand but generally cannot be applied as a result of contact with body-internal structures, for instance a wall of the body-internal cavity.

The shaft may be provided with a jacket, the latter for example providing a protective function or electrical insulation. In the case where the shaft comprises a rigid shaft tube, the shaft tube preferably consists of a metallic material, for instance stainless steel, and the jacket consists of a plastics material, which for instance may rest against the outer side of the shaft tube in the style of a shrink tubing. By way of example, the endoscopic instrument can be an electrosurgical instrument.

The endoscopic instrument may further comprise a handle with a movable part which may be connectable to a proximal end of the transmission element such that the tool is actuatable by actuating the movable part by means of a movement of the transmission element relative to the shaft. Preferably, the handle is releasably connectable to a proximal end of the shaft.

As a result of the sleeve and/or the coupling shaft being detachable from one another by way of a reversible change in the cross-sectional profile, detaching the coupling, and hence detaching the instrument insert from the shaft, is facilitated in a simple way. In particular, the cross-sectional change can be a cross-sectional deformation which can be brought about by a manual exertion of force by a user, as a result of which a particularly simple separation of the instrument insert from the shaft can be rendered possible. Moreover, as a result of a change in the cross-sectional profile being required to release the coupling, a secure hold of the instrument insert on the shaft can be facilitated without an additional anti-twist device. Consequently, detaching the instrument insert from the shaft can be facilitated in a simple way and, at the same time, an inadvertent detachment can be reliably prevented. As a result of it being possible to take the endoscopic instrument apart and the instrument insert being detachable from the shaft, cleaning and sterilization of the instrument and an interchange of the instrument insert can be simplified.

In the following disclosure, the invention is explained in particular on the basis of embodiments in which the distal end portion of the shaft comprises a sleeve or is in the form thereof, with the instrument insert comprising a coupling shaft that is insertable into the sleeve. However, it is understood that, in a corresponding reversed arrangement, the coupling shaft may be assigned to the shaft of the endoscopic instrument and the sleeve may be assigned to the instrument insert.

The endoscopic instrument according to the invention can be designed in such a way that a reversible change in the cross-sectional profile is likewise required to close the coupling. In particular, for connecting the instrument insert to the shaft, the coupling shaft may be insertable into the sleeve, with there possibly being a change in the cross-sectional profile, for example a cross-sectional deformation or change in size of the cross section, for the purposes of closing the coupling, said change in the cross-sectional profile being able to be the inverse of the change required to release the coupling. In this way, a fixed and secure connection of the instrument insert to the shaft can be achieved in a simple way.

Preferably, the reversible change in the cross-sectional profile for detaching the coupling shaft from the sleeve is a reversible deformation of the cross-sectional profile of the sleeve and/or of the coupling shaft, in particular an elastic deformation. The sleeve or the coupling shaft is consequently designed to be elastically deformable for the purposes of releasing the connection. Therefore, to release the connection of the instrument insert to the shaft, there is a need for a cross-sectional deformation of the sleeve or the coupling shaft against an elastic restoring force. In particular, the sleeve or the coupling shaft can be prestressed for holding the coupling shaft in the sleeve. This is advantageous in that the coupling is forced closed without the action of an external force and, further, the coupling shaft can be held particularly securely in the sleeve; furthermore, this can simplify closing the coupling.

In particular, the cross-sectional profile can be a substantially closed cross-sectional profile, that is to say the reversibly changeable cross-sectional profile has a substantially closed form in the circumferential direction, for example closed in ring-shaped fashion. Therefore, according to this embodiment, the sleeve and/or the coupling shaft has a substantially closed cross-sectional profile, at least in portions, said closed cross-sectional profile being reversibly changeable for detaching the coupling shaft from the sleeve, in particular reversibly changeable as a result of an elastic deformation. Here, and below, "substantially closed" means, in particular, that the portion of the sleeve or of the coupling shaft in which the cross-sectional profile is reversibly deformable comprises at least one sub portion in which the cross-sectional profile is circumferentially closed, for example closed in ring-shaped fashion. As a result, a particularly secure connection and a high bending loadability of the connection of the instrument insert to the distal end region of the shaft can be achievable.

According to one embodiment of the invention, the sleeve comprises a first holding structure and the coupling shaft comprises a second holding structure which interacts with the first holding structure for the purposes of holding the coupling shaft in the sleeve. The first and second holding structure consequently are designed for such interaction that the coupling shaft is held in the sleeve and, in particular, secured against release in the axial direction so that the instrument insert is connected to the shaft. Furthermore, according to this embodiment, the sleeve is convertible by a reversible, in particular elastic cross-sectional deformation from a work shape, in which the first holding structure and the second holding structure interact for the purposes of holding the coupling shaft in the sleeve, to an assembly shape, in which the first holding structure and the second holding structure are detached from one another. Alternatively or in addition, the coupling shaft can be convertible by a reversible, in particular elastic cross-sectional deformation from a work shape, in which the first and the second holding structure interact for holding the coupling shaft in the sleeve, to an assembly shape, in which the first and the second holding structure are detached from one another. To keep the connection, the sleeve and the coupling shaft therefore have a respective work shape, in which holding structures that correspond to one another interact for holding purposes, with the sleeve and/or the coupling shaft being able to be brought into an assembly shape by way of a reversible deformation for the purposes of releasing the connection. In particular, the first and/or the second holding structure is arranged for the purposes of interacting with the respectively corresponding holding structure in the respective work shape, and arranged separately from the latter in the assembly shape. Once the sleeve or the coupling shaft has been converted into the assembly shape by way of a reversible deformation, the coupling shaft is consequently removable from the sleeve. To insert the coupling shaft into the sleeve, that is to say for connecting the instrument insert to the sleeve or for closing the coupling, the sleeve and/or the coupling shaft can be brought from the assembly shape to the work shape. The sleeve and/or the coupling shaft can have a closed cross section, in particular in the region of the holding structure.

As a result of the sleeve comprising a first holding structure and the coupling shaft comprising a second holding structure, with the second holding structure interacting with the first for the purposes of holding the coupling shaft in the sleeve, it is possible, when the sleeve or the coupling shaft has the work shape, to facilitate a secure hold of the instrument insert on the shaft and hence facilitate safe operation with the endoscopic instrument. Further, a simple separation of the instrument insert from the shaft of the instrument can be facilitated when the sleeve or the coupling shaft has the assembly shape, for example for cleaning purposes or for an interchange of the instrument insert. What can be achieved in the case where the sleeve or the coupling shaft is convertible from the work shape into the assembly shape as a result of an elastic cross-sectional deformation is that the work shape is maintained without an external action and consequently the coupling remains reliably closed, that the coupling can be opened by a temporary cross-sectional deformation as a result of an external force acting against an elastic restoring force, and that, when there is no longer the action of an external force, the cross-sectional profile re-adopts the work shape as a result of elastic return to the original shape.

The shaft can advantageously have a cross section with an external contour that corresponds to the cross-sectional contour of the sleeve in the work shape, or for example a circular cross section which transitions into the cross section of the sleeve in the work shape in a transition portion of the sleeve and/or of the shaft. Provided the shaft has a rigid form, a rigid shaft tube, in particular, which forms an external shaft may have a cross section with a contour that corresponds to the cross-sectional contour of the sleeve in the work shape, or which transitions to the latter. In particular, the shaft tube may have a greater wall thickness than the sleeve but have a cross-sectional contour that corresponds to the cross-sectional contour of the sleeve in the work shape or that transitions thereto in the transition portion; by way of example, the shaft tube can be a section tube with a corresponding cross-sectional section. As a result this allows the shaft of the endoscopic instrument to have a largely smooth external contour.

According to an advantageous embodiment, provision is made for the first holding structure to extend over one or more partial angular ranges of the sleeve in the circumferential direction. Consequently, as seen from the longitudinal axis of the sleeve or of the coupling shaft, the first holding structure takes up one or more partial angular ranges, with however at least one free angular range not being taken up by the first holding structure. Alternatively or in addition, provision can be made for the second holding structure, to which the longitudinal axis relates, to extend over one or more partial angular ranges of the coupling shaft, with at least one free angular range not being taken up by the second holding structure. Further, the sleeve according to this embodiment comprises at least one pressure point for deforming the cross-sectional profile of the sleeve from the work shape into the assembly shape, with the at least one pressure point being situated outside of the partial angular ranges of the first and the second holding structure, that is to say situated in the at least one free angular range. Consequently, the at least one pressure point is offset in relation to the first or the second holding structure and may for example be arranged approximately in the center of a free angular range. Preferably, the at least one pressure point is located in an angular range in which the cross-sectional profile of the sleeve has a convex shape. In a particularly advantageous manner, the cross-sectional profile of the sleeve may be closed in ring-shaped fashion in at least one portion in the region of the first holding structure and may have a circumferentially convex form. In particular, the sleeve and the coupling shaft have such an embodiment that, as a result of the action of a compressive force from the outside in the radial direction, the cross-sectional profile of the sleeve is deformed in such a way that the first holding structure is lifted in the radial direction and thus separated from the second holding structure, and hence no longer interacts with the second holding structure for the purposes of holding the coupling shaft in the sleeve. To this end, a cavity may be provided in the region of the pressure point, between an outer surface of the coupling shaft and an inner surface of the sleeve, and said cavity may serve to allow the sleeve to be sufficiently compressed in the region of the pressure point.

According to an embodiment of the invention, the work shape of the sleeve is a flattened or flat form, for instance an elliptical or oval form, with one pressure point being arranged at each vertex of the flattened cross-sectional form and hence two pressure points that are at least approximately opposite one another in relation to the longitudinal axis are provided. The cross section of the sleeve consequently has a circumferentially convex external contour, at least in the region of the first holding structure, with the external contour respectively having a greater curvature in the region of the opposing vertices than in the regions situated therebetween, with the pressure points approximately being arranged in the regions of greatest curvature. By exerting a compressive force on the pressure points, the flattened shape can be pressed together from the vertices such that the flatter regions, which are located between the vertices and in which the first or the second holding structure is arranged, are at least partially displaced to the outside and as a result the cross-sectional profile adopts the assembly shape, in which the first holding structure is lifted off the second. By way of example, the assembly shape may likewise be a flattened shape, with the principal axis that connects the vertices being rotated through approximately 90° in relation to the work shape, but it may also be a circular shape or a flattened shape with the same principal axis as the work shape but with less flattening or ellipticity. This can reliably prevent an unintended detachment but nevertheless leaves the coupling conveniently detachable.

Alternatively, the work shape can be a circular shape, with the two pressure points being arranged opposite one another, and the assembly shape is a flattened, for instance elliptical or oval shape, in which the pressure points are located between the vertices in the circumferential direction, in particular approximately centrally between the vertices. Further alternatively, the work shape can be a flattened shape, with the pressure points being arranged between the vertices, the assembly shape being a flattened shape with the same principal axis but more pronounced flattening or ellipticity. This can also facilitate a simple detachment of the coupling by manual exertion of a compressive force on opposing pressure points.

According to a further embodiment of the invention, the sleeve comprises three pressure points which are in each case offset by approximately 120° from one another with respect to the longitudinal axis of the sleeve, with the cross-sectional profile or the cross-sectional contour preferably likewise being circumferentially convex. By exerting a compressive force on the three pressure points, it is possible to lift the respective regions of the cross-sectional shape, which are situated therebetween, in the radial direction such that the first and the second holding structure are separated from one another there. This can also easily facilitate a manual release of the connection, with particularly high reliability against an inadvertent release being achievable.

Preferably, the sleeve and/or the coupling shaft are formed in such a way that these are detachable from one another by exerting a compressive force on the at least one pressure point by a user using one or more fingers of their hand, the compressive force comfortably being able to be applied by the fingers but generally not being able to be applied by contact with body-internal structures. In particular, the compressive force may be exertable on two opposing pressure points using two fingers of a hand or on three pressure points offset by 120° using three fingers. In this case, a compressive force for example ranging from approximately 1 to 30 N, preferably ranging from approximately 3 to 10 N, in particular approximately 5 N, may be suitable for detaching the coupling shaft from the sleeve.

The sleeve or the coupling shaft may have the reversibly deformable cross-sectional profile overall or only in one or more portions. In particular, the sleeve may have a reversibly deformable cross section in a portion that extends up to a distal end of the sleeve or the coupling shaft may have a reversibly deformable cross section in a portion that extends up to a proximal end of the coupling shaft, in each case for detaching the coupling shaft from the sleeve. Then again, provision can also be made, for example, for the sleeve or the coupling shaft to be deformed only in a central portion for the purposes of detaching the coupling shaft from the sleeve, while a proximal end and a distal end are not deformed; in this case, the pressure point or points is/are arranged in the central portion.

According to an advantageous embodiment, the coupling shaft comprises a support portion for supporting an end portion of the sleeve in the work shape. In the case where the sleeve is assigned to the shaft, the end portion of the sleeve is a distal end portion, and in the case where the sleeve is assigned to the instrument insert, said end portion is a proximal end portion. By way of example, the support portion can be arranged in the distal end region of the coupling shaft in the first case and in the proximal end region thereof in the second case. In particular, the support portion has an external contour which at least approximately corresponds to the internal contour of the sleeve in the corresponding end portion when in the work shape.

As a result, the sleeve is supported at its corresponding end portion in the work shape such that the sleeve can only be deformed in a central portion for the purposes of detaching the coupling shaft from the sleeve. What this can achieve is that despite the cavity within the sleeve required for deformation purposes, the coupling has significant rigidity against a lateral load, even in the corresponding direction.

Advantageously, the first holding structure can be in the form of an engagement structure and the second holding structure can be in the form of an engagement element designed to engage in the first holding structure, or conversely the second holding structure can be in the form of an engagement structure and the first holding structure can be in the form of an engagement element designed to engage in the second holding structure. The engagement structure in particular has an undercut, as seen from a distal axial direction, and may be formed for example by a slot or perforation extending in the circumferential direction or by a groove extending in the circumferential direction. The engagement element is arranged protruding inward from the sleeve or outward from the coupling shaft, especially in the radial direction, and may in particular be formed as an annular collar or stud, for example as a bayonet element; consequently, as seen from the proximal axial direction, the engagement element may have an undercut. Consequently, the engagement element engages in the engagement structure in the work shape such that the coupling shaft is held in the sleeve. The engagement element is detached from the engagement structure in the assembly shape such that the coupling shaft is able to be taken from the sleeve. In a particularly advantageous manner, the sleeve and/or the coupling shaft may have a closed cross-sectional profile, possibly closed apart from the engagement structure itself, at least in a portion in which the engagement structure or the engagement element is arranged. In this way, a particularly secure, in particular interlocking connection can be attained between the base of the instrument insert and the shaft.

According to one embodiment of the invention, the second holding structure comprises at least one stud radially protruding above a surface of the coupling shaft and the first holding structure comprises at least one cut-out corresponding therewith or a slot extending in the circumferential direction or else a groove extending in the circumferential direction, with the at least one stud being designed and arranged for engagement in the corresponding cut-out or slot. Consequently, the stud represents an engagement element and the cut-out or the slot or the groove represents a corresponding engagement structure. In particular, the work shape of the sleeve and/or of the coupling shaft can be designed in such a way that the at least one stud engages in the cut-out or slot and the coupling shaft is held in the sleeve as a result, and the assembly shape of the sleeve and/or of the coupling shaft can be designed in such a way that the at least one stud does not engage in the cut-out or slot such that the coupling shaft is detachable from the sleeve. According to a variant of this embodiment, the at least one stud engages in the second holding structure in such a way that the stud is able to be pressed in manually from an outer side of the sleeve and as a result the coupling shaft can be converted into the assembly shape. As a result, particularly high dependability against an inadvertent release of the coupling can be achievable.

According to an advantageous embodiment of the invention, the first and the second holding structure interact for holding the coupling shaft in the sleeve so as to be secured against rotation. In particular, the first and the second holding structure are designed in such a way that when the engagement element engages in the engagement structure, the coupling shaft is held not only against a removal from the sleeve in the axial direction, but also against a rotation about the longitudinal axis. To this end, an engagement element for example in the form of a radially protruding stud and an engagement structure in the form of a groove extending in the circumferential direction may have extents in the circumferential direction that correspond to one another. By way of example, these may also be adapted to one another in such a way that a rotation about a restricted angle of rotation is admissible and corresponding stops in the circumferential direction are provided on both sides. What this can achieve is that the tool is particularly securely connected to the shaft and has an alignment controllable by way of a rotation of the shaft about its longitudinal axis. However, free rotatability of the coupling shaft about the longitudinal axis may alternatively also be achievable by way of a circumferential form of the engagement structure and/or the engagement element.

According to a further embodiment of the invention, the first and/or the second holding structure has an oblique shoulder in a circumferential direction, on one side or on both. As a result of rotating the sleeve relative to the coupling shaft, it is consequently possible to lift the first holding structure in the radial direction and/or press the second holding structure down in the radial direction by way of the corresponding oblique shoulder. In this way, the sleeve and/or the coupling shaft can be converted from the work shape into the assembly shape by way of a rotation of the sleeve relative to the coupling shaft. This has a further advantage that, as a result of a rotation and a subsequent axial movement of the base of the instrument insert relative to the shaft, the instrument insert can be detached from the shaft, which approximately corresponds to the movement when releasing a bayonet connection. In particular, the sleeve and the coupling shaft can be designed in such a way that a deformation of the cross-sectional profile of the coupling shaft or of the sleeve is forced when the coupling is connected by the rotational movement, and the coupling shaft and the sleeve latch against one another after a corresponding angular position has been reached. As a result, this can create a connection which is particularly simple to release and at the same time is largely secured against an inadvertent release.

Preferably, the coupling shaft has a resilient lug and the sleeve has a cut-out, in which a detent of the lug can engage for holding the coupling shaft in the sleeve so as to be secured against rotation. In particular, the detent can engage in the cut-out in such a way that the former can be pressed in from the outside by hand so that the sleeve is rotatable relative to the coupling shaft after said detent has been pressed in. Particularly in the case of the aforementioned embodiment, in which the coupling can be released by rotation of the sleeve relative to the base of the instrument insert, this can achieve further increased dependability against an inadvertent detachment.

Advantageously, provision can be made in the axial direction for the first and/or the second holding structure to have an oblique shoulder in an insertion direction. Such a running-in geometry can for example be formed by a ramp that rises in that axial direction in which the coupling shaft is introduced into the sleeve for the purposes of closing the coupling, or by corresponding wings. By way of the oblique shoulder, the cross-sectional profile of the coupling shaft and/or of the sleeve can for example be deformed, in particular against an elastic restoring force, in such a way when the coupling shaft is inserted that the coupling to the sleeve can be closed without exerting an external force and an external action of force is only required to release the coupling. In particular, the sleeve and the coupling shaft can be designed in such a way that a deformation of the cross-sectional profile of the coupling shaft or of the sleeve is forced when the coupling is connected by the axial movement, and the coupling shaft and the sleeve latch against one another after a corresponding axial position has been reached. This can further simplify the assembly of the endoscopic instrument.

According to a further embodiment of the invention, the first and the second holding structures may comprise interacting friction surfaces and/or be designed for micro-teeth. What the friction surfaces or the micro-teeth can achieve is that the coupling shaft is held in the sleeve by force fit. In this way, the instrument insert can likewise be held easily and securely on the shaft and be detachable from the latter. Such a connection by means of friction or micro-teeth may be provided, in particular as an alternative or in addition to the above-described connection by means of the engagement elements and engagement structures.

Preferably, the sleeve and/or the coupling shaft at least partly consist of metallic glass. In particular, the reversibly deformable portion of the sleeve or of the coupling shaft may be manufactured from metallic glass. As a result of using metallic glass, great elastic deformability and, at the same time, long-term durability may be achievable. Alternatively, the sleeve and/or the coupling shaft may for example at least partly consist of spring steel.

According to a further embodiment of the invention, the cross-sectional profile of at least the sleeve is changeable for detaching the coupling shaft from the sleeve by the action of temperature. According to this embodiment, the connection between the base of the instrument insert and the shaft can be designed, for example, in the style of a shrink-fit chuck. In particular, provision can be made for the sleeve and the coupling shaft to each have an approximately cylindrical form, at least in the portion in which the cross-sectional profile is reversibly changeable, the external radius of the coupling shaft and the internal radius of the sleeve being chosen in such a way that the coupling shaft is held securely in the sleeve if both the coupling shaft and the sleeve have a working temperature ranging between approximately 30° C. and 40° C., and that the coupling shaft is detachable from the sleeve by heating the sleeve to an assembly temperature. A secure, detachable connection between the instrument insert and the shaft can also be achievable in this way.

A coupling according to the invention for detachably connecting an instrument insert to the shaft of an endoscopic instrument comprises two interacting coupling parts, specifically a coupling sleeve, shortened here to sleeve, and a coupling shaft which are releasably connectable to one another. The sleeve can be arrangeable at a distal end portion of the shaft and the coupling shaft can be arrangeable at a proximal end region of a base of the instrument insert, or the coupling shaft can be arrangeable at the distal end portion of the shaft and the sleeve can be arrangeable at a proximal end region of the base, or represent the latter. Therefore, the sleeve and/or the coupling shaft has a preferably substantially closed cross-sectional profile, at least in portions, said closed cross-sectional profile being reversibly changeable for detaching the coupling shaft from the sleeve, in particular changeable as a result of an elastic deformation. By way of example, the sleeve can comprise a first and the coupling shaft can comprise a second holding structure, the sleeve and/or the coupling shaft being convertible by reversible deformation from a respective work shape, in which the first holding structure is arranged with the second holding structure for holding the coupling shaft in the sleeve, to a respective assembly shape, in which the first holding structure and the second holding structure are arranged separate from one another. In particular, the sleeve and the coupling shaft may be in the form already described above. As a result of this, it is possible to facilitate a secure connection of the two coupling parts, with no additional anti-twist device being required, and a simple detachment of the coupling parts from one another.

The present invention furthermore relates to a shaft for an endoscopic instrument, and further to an instrument insert for an endoscopic instrument. The endoscopic instrument is a medical endoscopic instrument in particular, for example a surgical endoscopic instrument.

A shaft according to the invention is elongate and, in particular, designed to be inserted into a body-internal cavity of a human or animal body. The shaft preferably is rigid or substantially rigid and comprises an elongate shaft tube but can also have a flexible design. At its proximal end, the shaft can be connectable to a handle or comprise the latter. According to the invention, the distal end portion of the shaft of the endoscopic instrument is in the form of a sleeve or coupling shaft, the sleeve or the coupling shaft having at least in sections a preferably substantially closed cross-sectional profile, which is reversibly deformable, in particular by way of an elastic deformation. In particular, the sleeve or the coupling shaft can be designed as described above in relation to reversible deformation of the cross-sectional profile. As a result, an instrument insert of an endoscopic instrument, which may be designed as described above, can easily be detachably connectable to the shaft.

According to exemplary embodiments of the shaft according to the invention, the sleeve or the coupling shaft may comprise a holding structure, the sleeve or the coupling shaft being convertible by way of a reversible, in particular elastic deformation from a work shape, in which the holding structure is arranged for interaction with a corresponding holding structure of an instrument insert of the endoscopic instrument, into an assembly shape, in which the holding structure is arranged separately from the corresponding holding structure of the instrument insert. Thus, for instance, in the case where the distal end portion of the shaft is designed as a sleeve, the holding structure of the sleeve can be arranged with a greater distance in the radial direction from a longitudinal axis of the sleeve in the assembly shape than in the work shape. Further, in the case where the distal end portion of the shaft is designed as a coupling shaft, the holding structure of the coupling shaft can be arranged with a shorter distance in the radial direction from the longitudinal axis of the sleeve in the assembly shape than in the work shape.

An instrument insert according to the invention comprises a tool which is designed to carry out endoscopic manipulations in a body-internal cavity in particular and preferably a shaft-shaped base. The tool preferably comprises at least one tool element that is movable relative to the base. The instrument insert may comprise an elongate transmission element, by means of which the tool is actuatable. According to the invention, a proximal end region of the base of the instrument insert is in the form of a sleeve or coupling shaft, the sleeve or the coupling shaft having at least in sections a substantially closed cross-sectional profile in particular, which is reversibly deformable, in particular by way of an elastic deformation. In particular, the sleeve or the coupling shaft can be designed as described above in relation to reversible deformation of the cross-sectional profile. As a result, the instrument insert can easily be detachably connectable to a shaft of an endoscopic instrument, which may be designed as described above.

According to exemplary embodiments of the instrument insert according to the invention, the sleeve or the coupling shaft may comprise a holding structure, the sleeve or the coupling shaft being convertible by way of a reversible, in particular elastic deformation from a work shape, in which the holding structure is arranged for interaction with a corresponding holding structure of a shaft of the endoscopic instrument, into an assembly shape, in which the holding structure is arranged separately from the corresponding holding structure of the shaft. By way of example, in the case where the proximal end region of the base is designed as a sleeve, the holding structure of the sleeve can be arranged with a greater distance in the radial direction from a longitudinal axis of the sleeve in the assembly shape than in the work shape. Further, for example in the case where the proximal end region of the base is designed as a coupling shaft, the holding structure of the coupling shaft can be arranged with a shorter distance in the radial direction from the longitudinal axis of the sleeve in the assembly shape than in the work shape.

According to a method according to the invention for taking apart an endoscopic instrument designed as described above, in which the sleeve and/or the coupling shaft is convertible by way of a reversible deformation from a respective work shape into a respective assembly shape, the cross section of the sleeve and/or of the coupling shaft is converted from the work shape into the assembly shape by the action of an external force. In particular, the exertion of a compressive force in the radial direction on one or more pressure points allows the cross section of the sleeve to be deformed in such a way that the holding structures that interact with one another for holding the coupling shaft in the sleeve are separated from one another. Alternatively, the sleeve and/or the coupling shaft can be deformed in such a way that the corresponding holding structures are lifted off one another, for example by rotating the sleeve over oblique shoulders directed in the circumferential direction. The coupling shaft is then taken from the sleeve in the axial direction and the instrument insert is separated from the shaft as a result; optionally, an elongate transmission element is pulled out of the shaft in the process. The method according to the invention may comprise further steps, for instance the removal of a handle. As a result, the endoscopic instrument can be taken apart after use, for the purposes of cleaning and sterilization, or a further instrument insert can be connected to the shaft.

To provide the endoscopic instrument before use, an instrument insert and a shaft of the endoscopic instrument, designed as described above, can be interconnected by way of an axial movement, with the coupling shaft being inserted into the sleeve and, for example, a holding structure of the instrument insert and a holding structure of the shaft being brought into engagement; optionally, an elongate transmission element of the instrument insert is simultaneously introduced into the shaft in the process. A cross-sectional deformation of the sleeve and/or of the coupling shaft as a result of an external manual application of force may be required for the insertion of the coupling shaft into the sleeve so that an assembly shape is reached; the axial movement may be sufficient to this end in the case where at least one of the holding structures has an oblique shoulder in the insertion direction, with a cross-sectional deformation into the assembly shape being forced. After an axial position has been reached and an optional rotation of the coupling shaft relative to the sleeve about the longitudinal axis has been carried out so that the corresponding holding structures of the sleeve and of the coupling shaft are only still separated from one another in the radial direction, a manual application of force from the outside or elastic restoring forces convert the cross section of the sleeve and/or of the coupling shaft into the respective work shape such that the holding structures interact with one another and the coupling shaft is held in the sleeve. Consequently, the instrument insert is connected to the shaft. Further, a handle can be placed against a proximal end of the shaft and can be connected to both a shaft tube and optionally the transmission element.

In the case where the cross-sectional profile of the sleeve and/or of the coupling shaft in the endoscopic instrument is changeable by the action of temperature for the purposes of detaching the coupling shaft from the sleeve, the sleeve is heated to an assembly temperature and the coupling shaft is subsequently introduced into the sleeve for the purposes of providing the instrument. After the sleeve has cooled the coupling shaft is securely held in the sleeve and consequently the instrument insert is connected to the shaft. To take apart the instrument, the sleeve is heated back up to the assembly temperature and widened as a result such that the coupling shaft can be removed from the sleeve. As mentioned above, further steps may be provided for the provision or taking apart of the instrument.

It is understood that the features mentioned above and the features yet to be explained below are applicable not only in the respectively specified combination but also in other combinations or on their own, without departing from the scope of the present invention.

BRIEF DESCRIPTION OF THE DRAWINGS

Further aspects of the invention emerge from the following description of preferred exemplary embodiments and the attached drawing, in which.

DETAILED DESCRIPTION OF THE REPRESENTATIVE EMBODIMENTS

Figure 1:
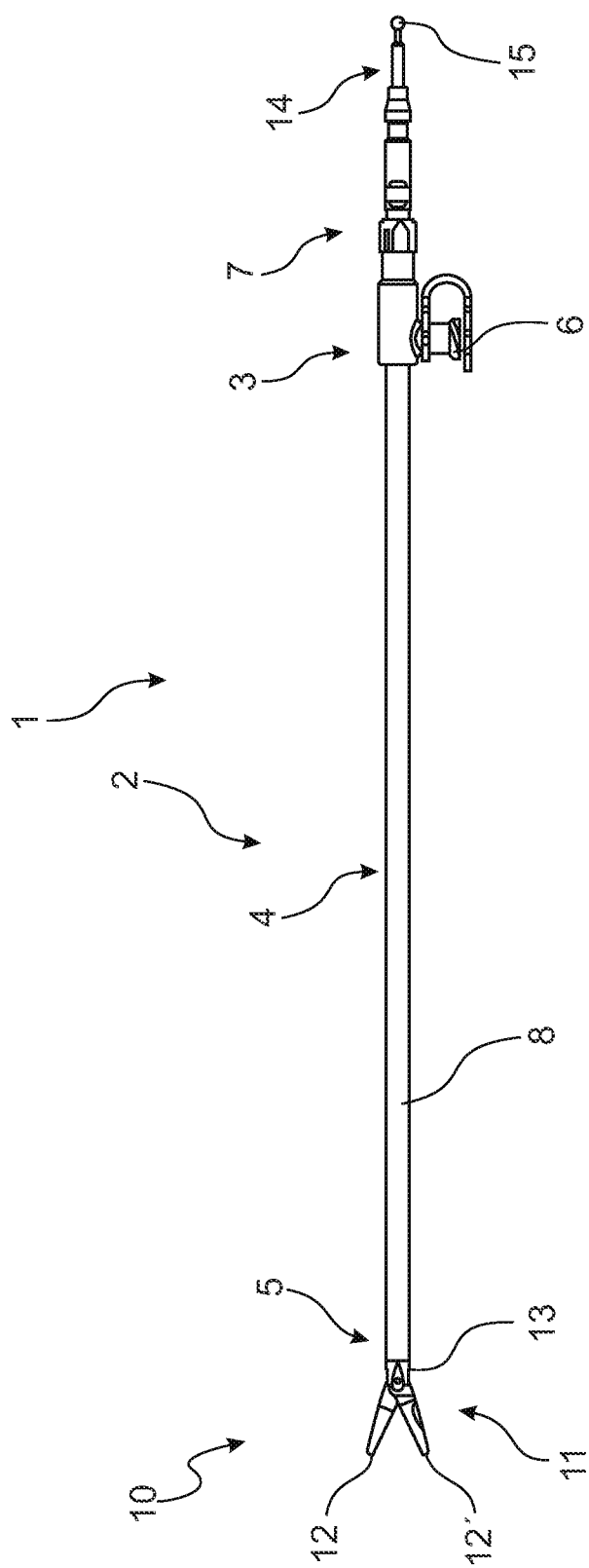
FIG. 1 shows a side view of an endoscopic instrument according to an embodiment of the present invention.

As illustrated in FIG. 1, a medical endoscopic instrument 1, according to an exemplary embodiment of the present invention, comprises a shaft 2 and an instrument insert 10. The shaft 2 comprises a proximal portion 3, an elongate central portion 4 and a distal end portion 5. The shaft 2 is dimensioned for insertion into a body-internal cavity, for example for insertion into a work channel of an endoscope which is introduced into the body-internal cavity during an endoscopic intervention. The proximal portion 3 of the shaft 2 may for example comprise a rinsing connector 6 and a connecting mechanism 7 for a connection to a handle not illustrated here. By means of the connecting mechanism 7, the handle can be connected to the shaft 2 so as to be rotatable or so as to be secured against rotation.

A tool 11 is arranged at the distal end portion 5 of the shaft 2 and is formed in the illustrated exemplary embodiment as a pair of scissors with two scissor blades 12, 12' that are pivotable relative to the distal end portion 5 of the shaft 2. The tool 11 is part of the instrument insert 10, which is inserted into the shaft 2 at the distal side. The instrument insert 10 furthermore comprises a base 13, formed on the distal side as a fork, in which the scissor blades 12, 12' are mounted in pivotable fashion. By way of a coupling shaft, the base 13 is inserted into the distal end portion 5 of the shaft 2 and connected to the latter, for the purposes of which the distal end portion 5 is formed as a sleeve as explained in exemplary fashion below.

A connecting rod 14 is arranged within the shaft 2 so as to be displaceable in the longitudinal direction of the shaft 10. The proximal end of the connecting rod 14 is formed by a connecting element, for example a ball 15, which can be connected to a movable part of the handle (not depicted here) for the purposes of displacing said connecting rod 14 in the longitudinal direction by actuating the movable part of the handle. The connecting rod 14 can transmit both tensile and shearing forces in the longitudinal direction of the shaft 10. The connecting rod 14 is connected to the scissor blades 12, 12' in articulated fashion and likewise forms a part of the instrument insert 10. The scissor blades 12, 12' can be opened or closed by displacing the connecting rod 14 in the proximal or distal direction. The shaft 2 is in the form of a metallic shaft tube which is enclosed by an electrically insulating jacket 8. By way of example, electrical connectors for RF voltage may be arranged on the handle or on the shaft 2.

Figure 2:
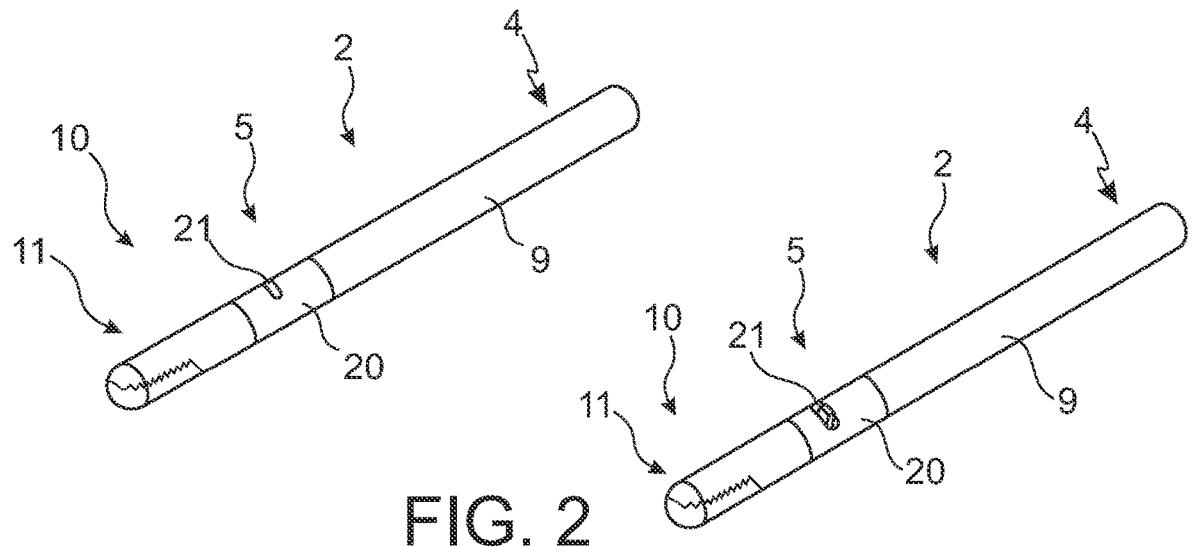
FIG. 2 shows a partial view of an endoscopic instrument according to a further embodiment of the invention.

FIG. 2 shows a shaft 2 according to a further exemplary embodiment of the invention in a partial view seen obliquely from the distal direction. As indicated in FIG. 2, the central portion 4 of the shaft is formed by a metal shaft tube 9; the jacket 8 (see FIG. 1) is not depicted. The distal end portion 5 of the shaft 2 is designed as a sleeve 20, which forms part of a coupling for detachably connecting the instrument insert 10 to the shaft 2. The sleeve 20 has two transverse slots 21, 21' which are arranged opposite one another and each extend in the circumferential direction, of these, only the upper transverse slot 21 is visible in FIGS. 2 and 3. The terms "above" and "horizontal" and "vertical" relate here and below to the relative position of the instrument depicted in the figures, the endoscopic instrument being able to adopt any other relative position when in use.

The sleeve 20 is elastically deformable at least in the region of the transverse slots 21, 21' such that the sleeve can adopt different cross-sectional shapes as a result of an external application of force in the radial direction. Consequently, the sleeve 20 has an elastically deformable cross-sectional profile in the region of the transverse slots 21, 21'. The sleeve 20 has an assembly shape in the left-hand image of FIGS. 2 and 3 while it has a work shape in the right-hand image of FIGS. 2 and 3. On the proximal side, the sleeve 20 is securely connected to the shaft tube 9 or can be formed in one piece with the shaft tube 9 such that an external contour of the shaft tube 9 merges smoothly into that of the sleeve 20.

In the proximal portion, the sleeve 20 has a largely unchanging cross-sectional form that approximately corresponds to the, e.g., circular or oval cross section of the shaft tube 9. However, the sleeve 20 is elastically deformable in the region of the transverse slots 21, 21' and to the distal side of the transverse slots 21, 21' and, if there is no external application of force, adopts the work shape or is elastically pretensioned into the work shape. As is evident in FIG. 3 at the distal end surface 22 of the sleeve 20, the work shape (right-hand image of the sleeve 20) is circular or a horizontal oval, that is to say has a horizontally directed semimajor axis, in the depicted example. As a result of the external application of force in the radial direction on surface regions, only one of which being visible in FIGS. 2 and 3, that are opposite one another in the horizontal direction, said surface regions being offset by approximately 90° in relation to the center of the transverse slots 21, 21' in the circumferential direction and being referred to here as pressure points 23, 23', the sleeve 20 can be deformed in such a way that it adopts the assembly shape which is a vertical oval in the illustrated example, that is to say has a vertically directed semimajor axis (left-hand image of the sleeve 20). The sleeve 20 is preferably produced from metallic glass, which facilitates both great durability and high elasticity.

The instrument insert 10 has a tool 11 which is in the form of grasping forceps in the depicted example, which comprise a stationary jaw part 16, which is securely connected to the base 13 of the tool, and a movable jaw part 16', which is articulated on the base 13 in pivotable fashion. A proximal end region of the base 13 is designed as a coupling shaft 17, arranged at the proximal end of which there are two studs 18, 18' opposite one another in the vertical direction, said studs each protruding beyond the surface of the coupling shaft 17 in the radial direction. The instrument insert 10 further comprises a connecting rod, not depicted, which is guided through the coupling shaft 17 and the base 13 and which is connected to the movable jaw part 16' and which is dimensioned for insertion into the shaft 2 of the endoscopic instrument 1 up to the proximal end thereof.

Figure 3:
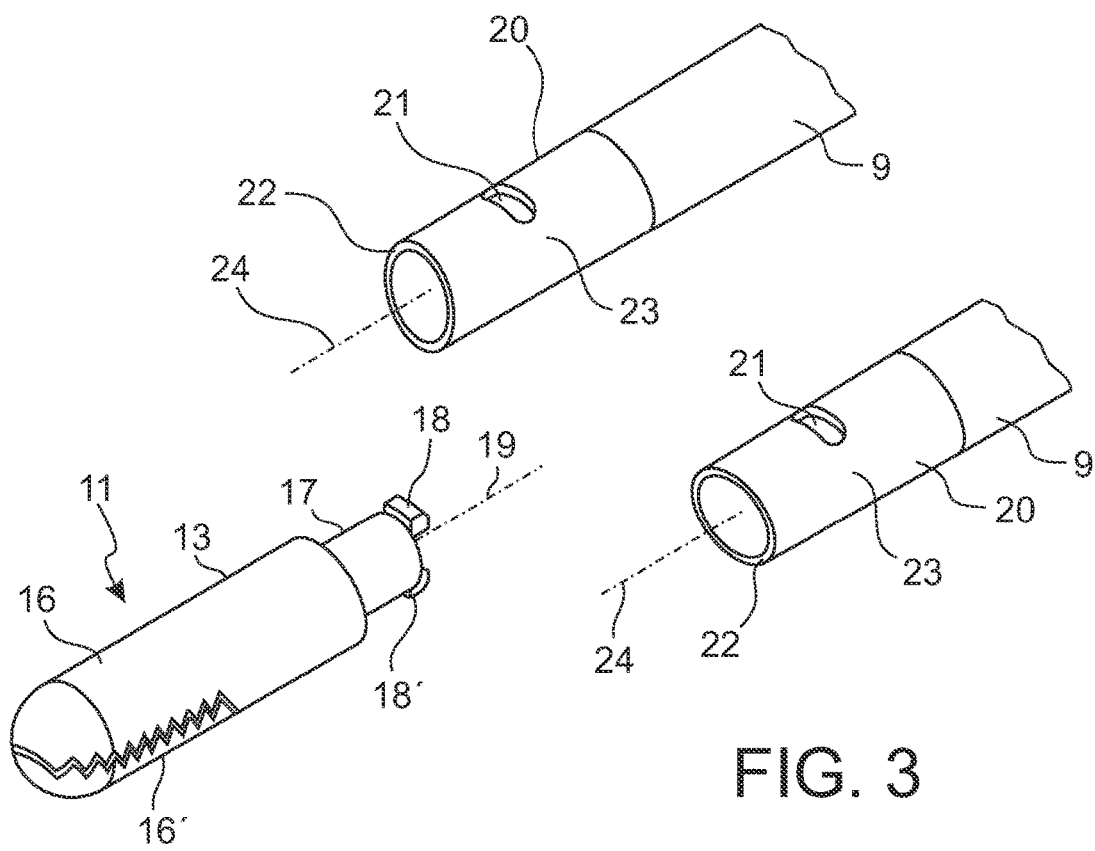
FIG. 3 shows the distal end region of the shaft of the instrument according to FIG. 2 with an instrument insert detached from the shaft.

The studs 18, 18' are formed in a manner corresponding to the transverse slots 21, 21' of the sleeve 20 such that the studs 18, 18' can engage in the transverse slots 21, 21' when the sleeve 20 has the work shape (right-hand image in FIGS. 2 and 3, with the stud 18 engaging in the transverse slot 21 being depicted in exaggerated fashion in the right-hand image in FIG. 2). Then again, in the assembly shape of the sleeve 20 (left-hand image of the shaft 2 in FIGS. 2 and 3), the vertical internal width of the sleeve 20 in the region of the transverse slots 21, 21' is greater than the diameter, measured in the vertical direction, of the engagement structure formed by the two studs 18, 18', that is to say greater than the vertical distance between the outer sides of the studs 18, 18'; therefore, the studs 18, 18' can no longer both simultaneously engage in the transverse slots 21, 21' in the assembly shape.

If the sleeve 20 is brought into the assembly shape by way of lateral pressure on the pressure points 23, 23' and if it is kept in said shape, the coupling shaft 17 can be inserted into the sleeve 20 until the studs 18, 18' are level with the transverse slots 21, 21' in the axial direction. If necessary, the studs 18, 18' can be brought into the angle positions corresponding to the transverse slots 21, 21' by way of a rotation of the coupling shaft 17 about its longitudinal axis. Then, the transverse slots 21, 21' are only still lifted off the studs 18, 18' in the radial direction. If the lateral application of force is subsequently terminated, the studs 18, 18' engage in the transverse slots 21, 21'. In this state, the coupling shaft 17 and hence the instrument insert 10 is securely held at the distal end of the shaft 2. As a result of the design of the transverse slots 21, 21' and the studs 18, 18', optionally additionally in conjunction with the base 13 resting against the distal end face 22 of the sleeve, an axial play can be restricted or avoided, just as this can optionally bring about a connection secured against rotation. As a result of renewed lateral pressure on the pressure points 23, 23', the sleeve 20 can be converted back into the assembly shape so that the sleeve 20 is lifted off the studs 18, 18' in the region of the transverse slots 21, 21' and the coupling shaft 17 can be pulled out of the sleeve 20 in the axial direction.

As is evident from FIGS. 2 and 3, a longitudinal axis 19 of the base 13 and the coupling shaft 17 is flush with a longitudinal axis 24 of the shaft 2 and the sleeve 20 in the assembled state, and the tool 11 is arranged on a distal-side continuation of the shaft 2.

Figure 4A:
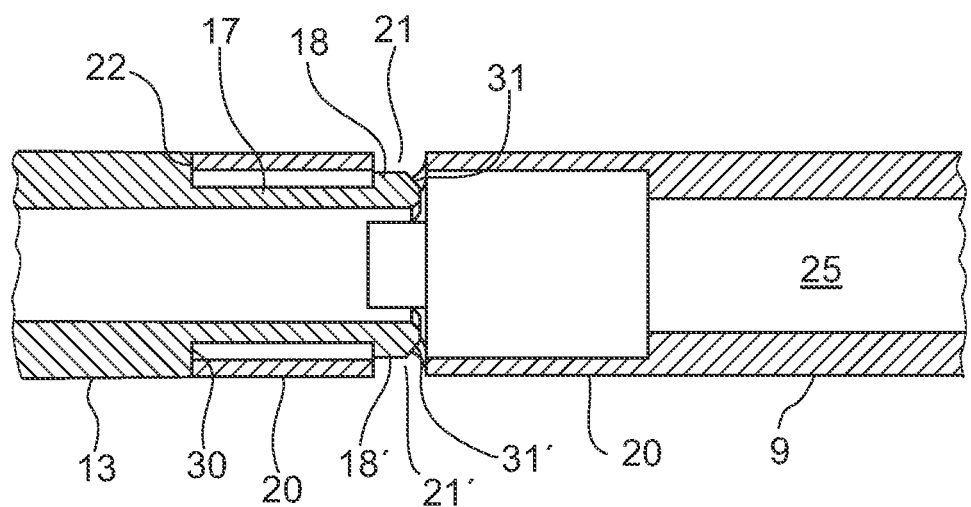
FIGS. 4a to 4c show the distal end region of the shaft of the instrument according to FIG. 2 with an inserted instrument insert with open and closed couplings in different representations.
Figure 4B:
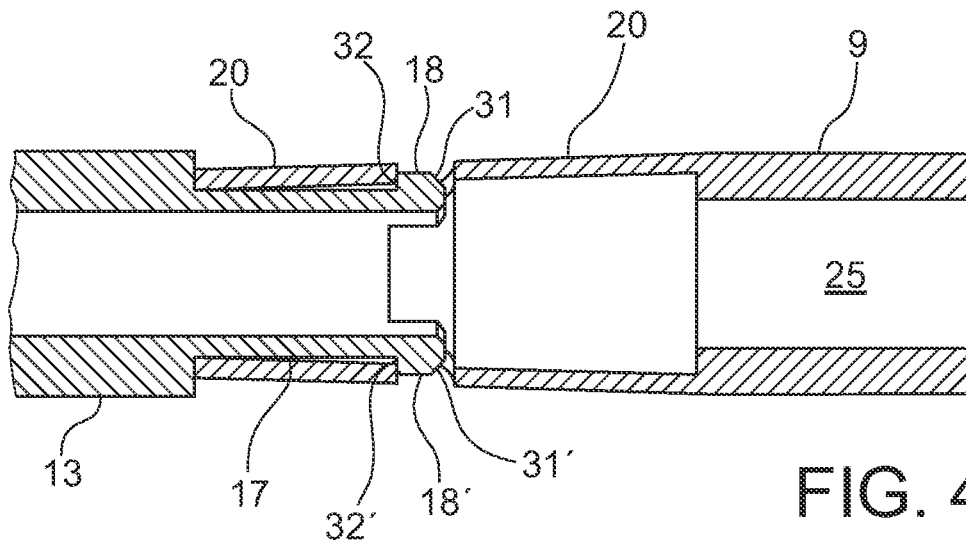

In FIGS. 4*a* and 4*b*, the coupling formed by the coupling shaft 17 and the sleeve 20 is shown in an open and closed state, respectively, in each case in a vertical longitudinal section. FIG. 4*a* shows that the coupling shaft 17 is inserted in the sleeve 20. In the case of the axially directed insertion movement, the sleeve 20 is widened in the vertical direction by way of proximal-side oblique shoulders 31, 31' of the studs 18, 18'. This simplifies the insertion of the coupling shaft 17 into the sleeve 20; additionally, a lateral compressive force can be exerted on the pressure points 23, 23' for the purposes of reaching and maintaining the assembly shape (see above). In the state shown in FIG. 4*a*, the coupling shaft 17 has been inserted so far into the sleeve 20 in the axial direction that a step 30 of the base 13 rests against the distal end face 22 of the sleeve 20. In this position, the studs 18, 18' are arranged radially within the transverse slots 21, 21'. FIG. 4*a* depicts the sleeve 20 in the assembly shape, in which the studs 18, 18' do not yet engage in the transverse slots 21, 21'.

FIG. 4*b* shows the sleeve 20 in the work shape, which the sleeve 20 assumes after reaching the position shown in FIG. 4*a* as a result of elastic restoring forces and optionally as a result of the discontinuation of the lateral compressive force. In the work shape, the studs 18, 18' engage in the transverse slots 21, 21' and the sleeve 20, by way of regions adjoining the transverse slots 21, 21' at the distal side, engages in the undercut formed by a distal-side step 32, 32' of the studs 18, 18'. As a result, the coupling shaft 17 and hence the base 13 of the instrument insert 10 is securely held on the shaft 2. In particular, an axial position of the base 13 relative to the shaft 2 is defined by the step 30 of the base 13, which acts as a stop, and the distal side of the studs 18, 18'. Further, a rotational position of the base 13 relative to the shaft 2 can be defined by the extent of the studs 18, 18' in the circumferential direction in conjunction with a corresponding extent of the transverse slots 21, 21'.

As is likewise evident in FIG. 4b, the sleeve 20 rests against the coupling shaft 17 in the vertical direction by means of an engagement portion, in particular at the distal end. As a result, this can achieve a connection of the base 13 to the shaft 2 that is rigid against corresponding bending loads. The base 13 with the coupling shaft 17 and also the sleeve 20 and the shaft tube 9 form an interior space 25 that is continuous in the longitudinal direction, the connecting rod, not depicted here, by means of which the tool 11 can be actuated, being guided therethrough. The shaft tube 9 has a greater wall strength than the sleeve 20 but an external contour that transitions smoothly into the external contour of the sleeve. The sleeve 20 can be formed in one part with the shaft tube 9.

Figure 4C:
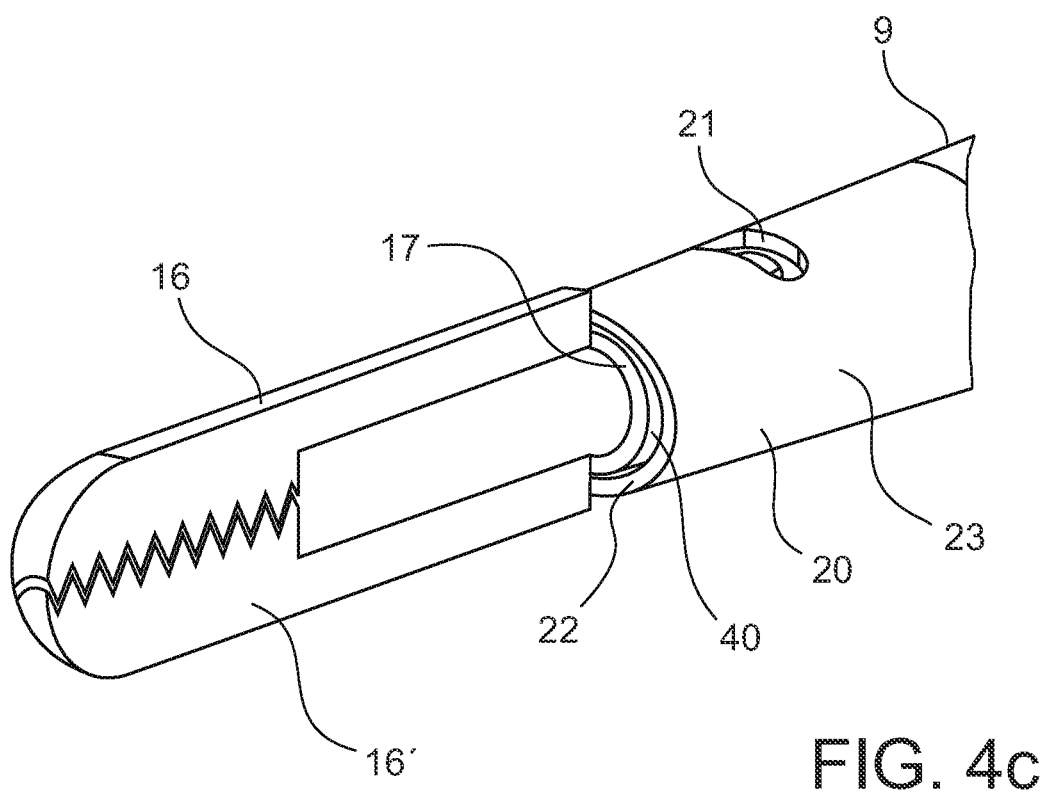

FIG. 4c shows a partly cut oblique view of the coupling in the closed state. As is evident from FIG. 4c, a cavity 40 is present in the region of the pressure point 23 between an external surface of the coupling shaft 17 and an inner surface of the sleeve 20, said cavity being present to allow the sleeve 20 to be pressed together sufficiently so that the studs 18, 18' can be detached from the transverse slots 21, 21'. A corresponding cavity is also present on the opposite side of the cross section that is not visible in FIG. 4c. In this exemplary embodiment, the coupling has a rigid form against a bending load in the horizontal direction by virtue of the distal end face 22 of the sleeve resting against the step 30 of the base 13 and being held by the distal-side step 32, 32' of the studs 18, 18', which each rest against the distal side of the relevant transverse slot 21, 21'; to this end, the relevant portions of the sleeve 20 and of the coupling shaft 17 are matched to one another with tight tolerance in respect of their length. The connecting rod and the mechanism for pivoting the movable jaw part 16' are not depicted in FIG. 4c.

Figure 5:
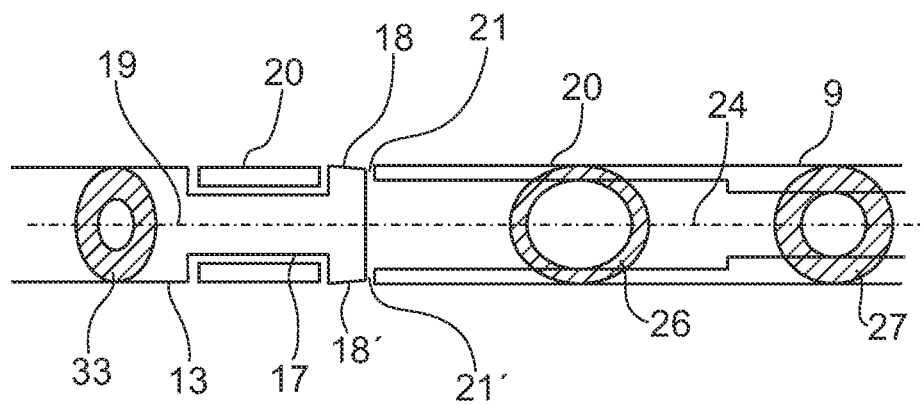
FIG. 5 shows a schematic representation of the distal end region of the shaft with instrument insert according to FIG. 4b in the longitudinal section, with indicated cross sections.

FIG. 5 shows a simplified schematic representation of the coupling in the closed state, that is to say corresponding to FIG. 4b, likewise in a vertical longitudinal section, with a plurality of cross sections being indicated for elucidation purposes. In the closed state of the coupling, in which the cross-sectional shape of the sleeve 20 is the work shape, the sleeve 20 with its regions adjoining the transverse slots 21, 21' on the distal side engages into the undercut formed by the distal-side step 32, 32' of the studs 18, 18', and the studs 18, 18' engage in the transverse slots 21, 21' (see FIGS. 4a and 4b). As indicated symbolically in FIG. 5, the sleeve 20 in the work shape has a horizontal oval cross section 26 in the region of the transverse slots 21, 21'. The shaft tube 9 which adjoins the sleeve 20 on the proximal side has a circular cross section 27. The base 13 likewise has a circular cross section 33.

Figure 6A:
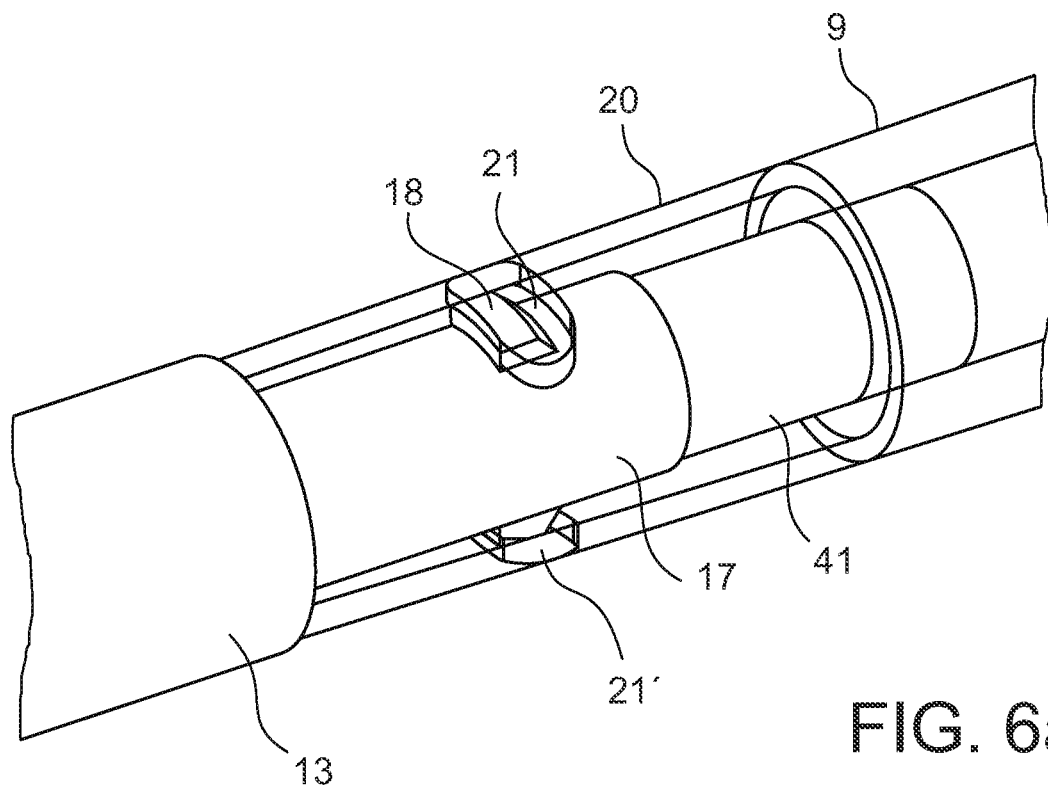
FIGS. 6a and 6b show two variants of the exemplary embodiment according to FIG. 2.
Figure 6B:
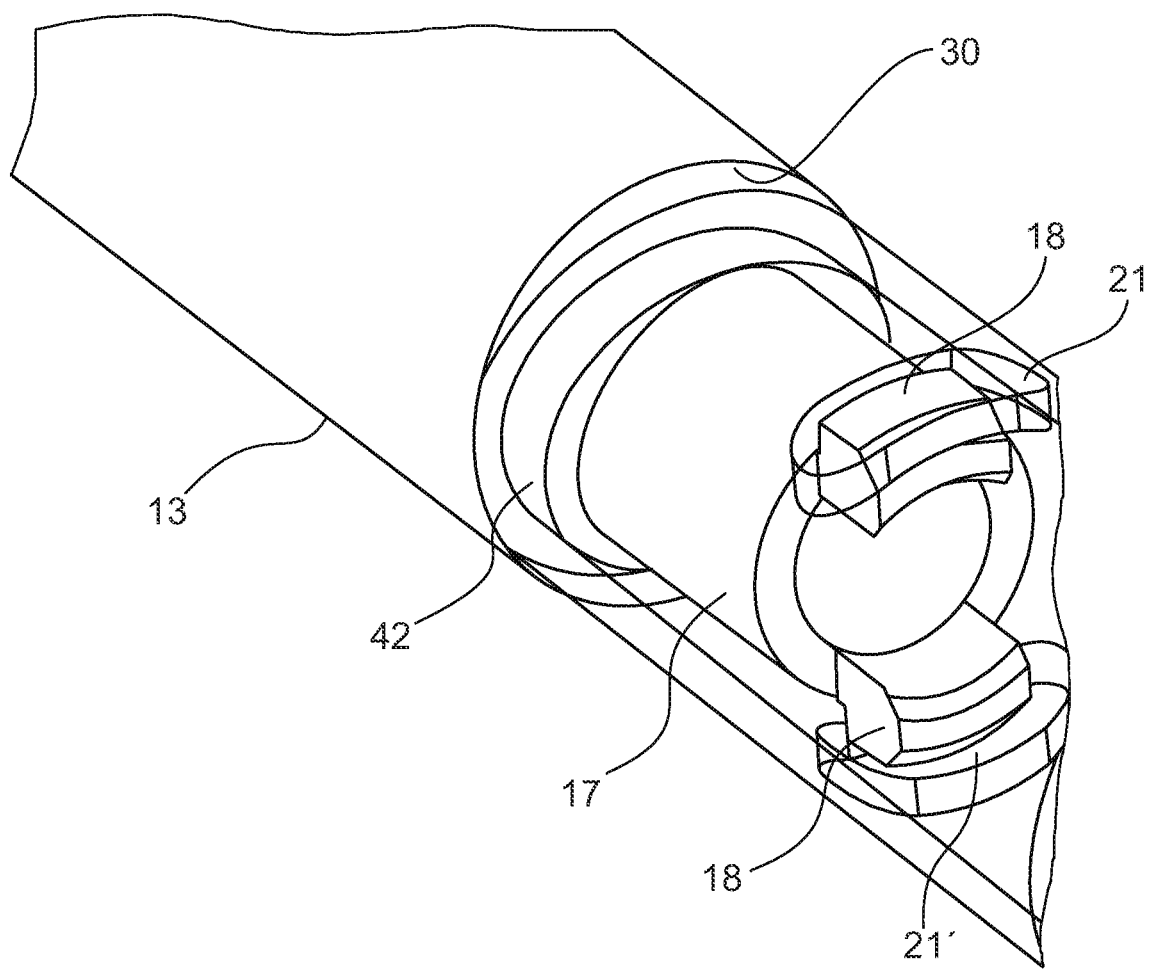

FIGS. 6a and 6b depict two variants of the exemplary embodiment described above, in each case in a partly transparent view. In the variant shown in FIG. 6a, the coupling shaft 17 has been extended in the proximal direction such that the latter protrudes through the sleeve 20 and into the shaft 9 in the closed state of the coupling. The proximal-side extension 41 of the coupling shaft 17 rests against the inner side of the shaft 9 with tight tolerances or without play. As a result, additional rigidity can be imparted on the coupling, especially in the horizontal direction as well.

In the variant depicted in FIG. 6b, the coupling shaft 17 has a support portion 42 on the distal side of the step 30 of the base 13, said support portion having a cross-sectional profile that is matched to the internal contour of the sleeve 20 in the work shape and rests against the latter without play. The support portion 42 only has a short longitudinal extent so as not to impede a deformation of the sleeve 20 for the purposes of detaching the studs 18, 18' from the transverse slots 21, 21'. Increased rigidity in the horizontal direction can also be attained in this way, the actuation profile 42 being able to represent an additional anti-twist device between the shaft 9 and the base 13.

Figure 7:
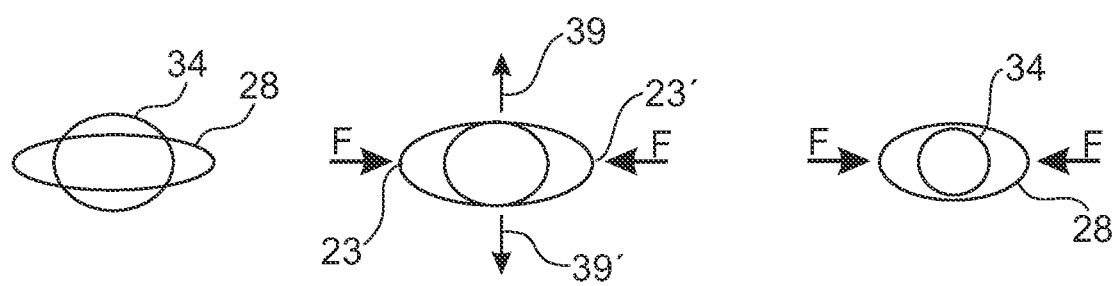
FIG. 7 shows a symbolic representation of the mode of action of the coupling according to one exemplary embodiment of the invention.

Opening the coupling is depicted symbolically by means of cross-sectional contours in FIG. 7. In the closed state (left-hand image), the cross-sectional contour 28 of the sleeve 20 is flattened in such a way in the region of a holding structure that the latter engages in an undercut of the coupling shaft 17, which is depicted with a circular cross-sectional contour 34. As a result of pressure from both sides (force F) on the pressure points 23, 23', which correspond to the vertices of the horizontal oval cross-sectional shape, the cross-sectional profile in the intervening circumferential regions can be spread in the direction of the arrows 39, 39' and hence the flattening of the cross section can be reduced (central image), until finally the holding structure of the sleeve is lifted out of the undercut of the coupling shaft 17 and the coupling is open (right-hand image).

Figure 8A:
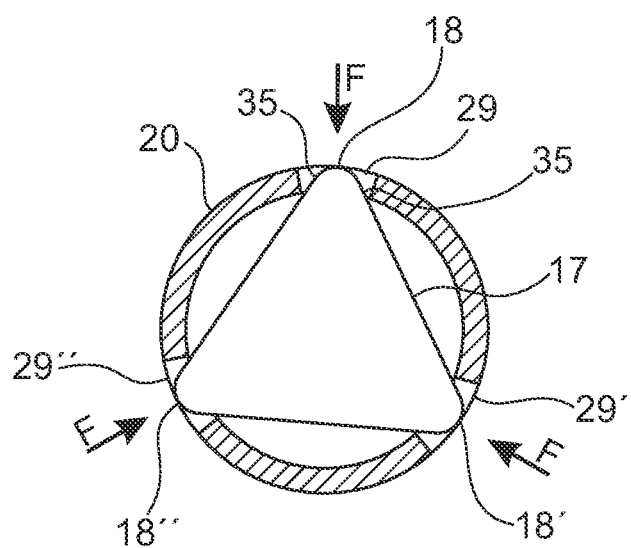
FIGS. 8a to 8c show a schematic representation of the mode of action of the coupling according to a further exemplary embodiment of the invention.
Figure 8B:
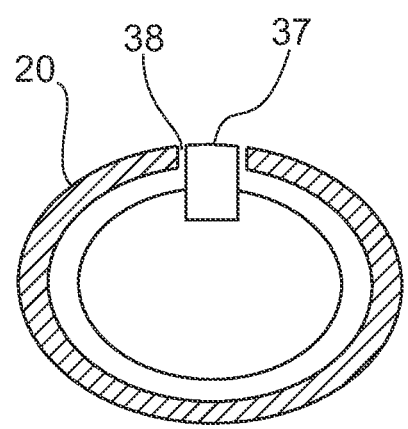
Figure 8C:
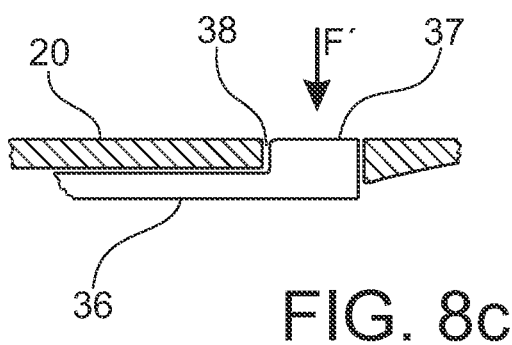

In a further exemplary embodiment of the invention, which is depicted schematically in FIGS. 8a to 8c, the coupling shaft 17 has a cross section which approximately has the shape of an equilateral triangle, the corners of the triangle being formed as studs 18, 18', 18" which, in the work shape, each engage in cut-outs 29, 29', 29" of the sleeve 20 that are in each case offset from one another by 120° in the circumferential direction. The coupling shaft 17 has such a deformable cross-sectional profile that the studs 18, 18', 18" can be pressed inward. The coupling can be released by virtue of a manual force F being exerted on the studs 18, 18', 18", in each case in the direction of the arrows, such that the coupling shaft 17 is converted into the assembly shape in which the studs 18, 18', 18" no longer engage in the cut-outs 29, 29', 29" and the coupling shaft 17 can be pulled out of the sleeve 20 in the axial direction (not depicted here). As in the exemplary embodiments described above, a force F of the order of one or a few N, for example approximately 5 N, may be sufficient for this here.

In the exemplary embodiment shown in FIG. 8a, the studs 18, 18', 18" each have, on both sides, oblique shoulders 35 in the circumferential direction. As an alternative or in addition to the manual application of the lateral compressive force, this provides the option of twisting the sleeve 20 relative to the coupling shaft 17 about the longitudinal axis, as a result of which the studs 18, 18', 18" are pressed-in in the radial direction by way of the respective oblique shoulders 35, and as a result likewise lose engagement with the cut-outs 29, 29', 29". The coupling can also be released thereby.

Further, alternatively or in addition, provision can be made for the sleeve 20 to have a deformable cross-sectional profile. In this case, the sleeve 20 can be deformed by a lateral application of force on pressure points, which are located between the cut-outs 29, 29', 29" in the circumferential direction, and by a rotation of the sleeve 20 relative to the coupling shaft 17 such that the studs 18, 18', 18" are detached from the cut-outs 29, 29', 29" (not depicted here).

According to a variant of the embodiment shown in FIG. 8a, the base 13 or the coupling shaft 17 further comprises a resilient lug 36 which carries a detent 37, which engages in a cut-out 38 of the sleeve 20 when the coupling is closed and which has no oblique shoulders in the circumferential direction (see FIGS. 8b, 8c). This therefore serves as an anti-twist device to prevent an inadvertent release of the coupling as a result of a torque that occurs when the instrument is used. Therefore, to release the coupling in this variant, the detent 37 must be pressed in by the application of a radial force F' in order to subsequently twist the coupling shaft 17 about the longitudinal axis relative to the sleeve 20.

For the sake of clarity, not all reference signs are shown in all of the figures. Reference signs not explained in connection with one figure have the same meaning as in the other figures.

Although the invention and its advantages have been described in detail, it should be understood that various changes, substitutions and alterations can be made herein without departing from the scope of the invention as defined by the appended claims. The combinations of features described herein should not be interpreted to be limiting, and the features herein may be used in any working combination or sub-combination according to the invention. This description should therefore be interpreted as providing written support, under U.S. patent law and any relevant foreign patent laws, for any working combination or some sub-combination of the features herein. Moreover, the scope of the present application is not intended to be limited to the particular embodiments of the process, machine, manufacture, composition of matter, means, methods and steps described in the specification. As one of ordinary skill in the art will readily appreciate from the disclosure of the invention, processes, machines, manufacture, compositions of matter, means, methods, or steps, presently existing or later to be developed that perform substantially the same function or achieve substantially the same result as the corresponding embodiments described herein may be utilized according to the invention. Accordingly, the appended claims are intended to include within their scope such processes, machines, manufacture, compositions of matter, means, methods, or steps.

LIST OF REFERENCE SIGNS

1 Instrument
2 Shaft
3 Proximal portion
4 Central portion
5 Distal end portion
6 Rinsing connector
7 Connecting mechanism
8 Jacket
9 Shaft tube
10 Instrument insert
11 Tool
12, 12' Scissor blade
13 Base
14 Connecting rod
15 Ball
16, 16' Jaw part
17 Coupling shaft
18, 18', 18" Stud
19 Longitudinal axis
20 Sleeve
21, 21' Transverse slot
22 End face
23, 23' Pressure point
24 Longitudinal axis
25 Interior space
26 Cross section
27 Cross section
28 Cross-sectional contour
29, 29', 29" Cut-out
30 Step
31, 31' Oblique shoulder
32, 32' Step
33 Cross section
34 Cross-sectional contour
35 Oblique shoulder
36 Lug
37 Detent
38 Cut-out
39, 39' Arrow
40 Cavity
41 Extension
42 Support portion
F, F' Force

The invention claimed is:

1. An endoscopic instrument having an elongate shaft and an instrument insert releasably connected to a distal end portion of the shaft, the distal end portion of the shaft being in the form of a sleeve and a proximal end region of a base of the instrument insert being in the form of a coupling shaft, or the distal end portion of the shaft being in the form of a coupling shaft and a proximal end region of a base of the instrument insert being in the form of a sleeve, with the coupling shaft being releasably held in the sleeve, wherein the sleeve and/or the coupling shaft at least in portions have a cross-sectional profile which is reversibly changeable for detaching the coupling shaft from the sleeve, the cross-sectional profile being reversibly changeable by an elastic deformation of the sleeve or coupling shaft for the purposes of detaching the coupling shaft from the sleeve;

the sleeve comprising a first holding structure and the coupling shaft comprising a second holding structure, the sleeve and/or the coupling shaft being convertible by reversible deformation from a respective work shape, in which the first holding structure is arranged with the second holding structure for holding the coupling shaft in the sleeve, to a respective assembly shape, in which the first holding structure and the second holding structure are arranged separate from one another;

the first and/or the second holding structure extending in the circumferential direction over one or more partial angular ranges of the sleeve or of the coupling shaft, and wherein the sleeve comprises at least one pressure point situated outside of the partial angular ranges, for deforming the cross-sectional profile of the sleeve, the coupling shaft having a support portion for supporting an end portion of the sleeve in the work shape, the support portion being spaced from an end of the coupling shaft, the support portion having a cross-sectional profile matched to an inner contour of the sleeve in the work shape, the coupling shaft being radially spaced from the sleeve in an area between the support portion and the first and second holding structures.

2. The endoscopic instrument of claim 1, wherein the cross-sectional profile is a closed cross-sectional profile.

3. The endoscopic instrument of claim 1, wherein the work shape of the sleeve is a flattened shape, with a respective pressure point being arranged in the vertices of the flattened shape, and/or the assembly shape of the sleeve is a flattened shape, with a respective pressure point being arranged between the vertices in the circumferential direction.

4. The endoscopic instrument of claim 1, wherein the sleeve has three pressure points, which are each offset by approximately 120° from one another.

5. The endoscopic instrument of claim 1, wherein the first holding structure is an engagement structure and the second holding structure is an engagement element embodied to engage in the first holding structure, or vice versa.

6. The endoscopic instrument of claim 5, wherein the second holding structure comprises a radially protruding stud and the first holding structure has a corresponding cut-out in which the stud engages.

7. The endoscopic instrument of claim 6, wherein the first and the second holding structure interact to hold the coupling shaft in the sleeve so as to be secured against rotation.

8. The endoscopic instrument of claim 1, wherein, the first and/or the second holding structure has or have an oblique shoulder in a circumferential direction, on one side or on both.

9. The endoscopic instrument of claim 1, wherein the coupling shaft has a resilient lug with a detent that engages in a cut-out of the sleeve.

10. The endoscopic instrument of claim 1, wherein, in the axial direction, the first and/or the second holding structure has an oblique shoulder in an insertion direction.

11. The endoscopic instrument of claim 1, wherein the first and the second holding structures comprise interacting friction surfaces and/or are designed for micro-teeth.

12. The endoscopic instrument of claim 1, wherein the sleeve and/or the coupling shaft at least partly consist of metallic glass.

13. An endoscopic instrument comprising:
an elongate shaft:
an instrument insert releasably connected to a distal end portion of the shaft;
the distal end portion of the shaft being in the form of a sleeve and a proximal end region of a base of the instrument insert being in the form of a coupling shaft, or the distal end portion of the shaft being in the form of a coupling shaft and a proximal end region of a base of the instrument insert being in the form of a sleeve;
the sleeve comprising a first holding structure, the coupling shaft comprising a second holding structure, the sleeve having a cross-sectional profile which is reversibly deformable from a respective work shape, in which the first holding structure is arranged with the second holding structure for holding the coupling shaft in the sleeve, to a respective assembly shape, in which the first holding structure and the second holding structure are arranged separate from one another;
the coupling shaft having a support portion for supporting an end portion of the sleeve in the work shape, the support portion is being spaced from an end of the coupling shaft, the support portion having a cross-sectional profile matched to an inner contour of the sleeve in the work shape, the coupling shaft being radially spaced from the sleeve in an area between the support portion and the first and second holding structures.

* * * * *